(12) United States Patent
Tsai et al.

(10) Patent No.: US 9,017,075 B1
(45) Date of Patent: Apr. 28, 2015

(54) BONE IMPLANT

(71) Applicant: Metal Industries Research & Development Centre, Kaohsiung (TW)

(72) Inventors: Tung-Lin Tsai, Kaohsiung (TW); Bo-Wei Pan, Kaohsiung (TW); Yi-Chin Chen, Kaohsiung (TW); Pei-Hua Wang, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 0 days.

(21) Appl. No.: 14/097,372

(22) Filed: Dec. 5, 2013

(51) Int. Cl.
*A61C 8/00* (2006.01)

(52) U.S. Cl.
CPC .............. *A61C 8/0022* (2013.01); *A61C 8/0057* (2013.01); *A61C 8/0068* (2013.01); *A61C 8/006* (2013.01)

(58) Field of Classification Search
CPC ................ A61C 8/0048–8/0078; A61C 8/0022
USPC .......... 433/172–176, 201.1; 623/17.17–17.18
See application file for complete search history.

(56) References Cited

U.S. PATENT DOCUMENTS

| | | | |
|---|---|---|---|
| 7,338,286 B2 | 3/2008 | Porter et al. | |
| 7,484,959 B2 | 2/2009 | Porter et al. | |
| 8,747,112 B2 * | 6/2014 | Brun | 433/173 |
| 2004/0101807 A1 | 5/2004 | Porter et al. | |
| 2004/0101808 A1 | 5/2004 | Porter et al. | |
| 2008/0102420 A1 | 5/2008 | Porter et al. | |
| 2009/0130629 A1 * | 5/2009 | Towse et al. | 433/174 |
| 2009/0136899 A1 | 5/2009 | Porter et al. | |

* cited by examiner

*Primary Examiner* — Edward Moran

(74) *Attorney, Agent, or Firm* — Alan D. Kamrath; Kamrath IP Lawfirm, P.A.

(57) ABSTRACT

A bone implant includes an implant having an implantation end and a connection end. A blind hole is formed in the connection end and extends in an axial direction, defining an abutment receiving section and a locking section. The abutment receiving section includes an anti-rotation portion having a minimal inner width perpendicular to the axial direction. An abutment includes an elastic, deformable portion, a connection portion, and a prosthesis engagement portion. The abutment further includes a bore extending in the axial direction. The elastic, deformable portion includes resilient plates, with a slit formed between two adjacent resilient plates. The elastic, deformable portion has a maximal outer width larger than the minimal inner width. The elastic, deformable portion is aligned and engages with the anti-rotation portion. An abutment screw includes a head end positioned in the bore of the abutment and a locking end engaged with the locking section.

6 Claims, 4 Drawing Sheets

BONE IMPLANT

BACKGROUND OF THE INVENTION

1. Field of the Invention

The present invention relates to an implant and, more particularly, to a bone implant that can be implanted into a bone.

2. Description of the Related Art

Generally, biting and chewing functions will be adversely affected if a tooth defect resulting from either aging or accidental impact is not restored. In severe cases, after effects, including forward declination of a tooth behind the location of a missing tooth, shrinkage of bone, and a change of the face shape, occur. Among various methods for tooth restorations, tooth implantation is becoming more and more popular due to the advantages of the lack of harm to natural teeth on two sides of the location of the missing tooth, of being easy to clean, of not causing feeling of a foreign substance, and of an aesthetic appearance after implantation.

Tooth implantation includes implanting a dental implant made of a medical grade material (such as titanium or ceramic) into an alveolar bone of a patient in a surgery. After bone integration, a dental crown is mounted to the tooth implant to restore the tooth of the patient for chewing and aesthetic purposes. The dental implant includes an implant and an abutment. The implant is implanted into the alveolar bone of the patient, the abutment is mounted to an end of the implant, and the dental crown is fixed to the abutment.

To assure reliably fixing of the abutment to the end of the implant, common dental implants nowadays generally have three pieces. Specifically, a blind hole extends axially from an end of the implant, and the abutment includes an axially extending bore. After the abutment is inserted into the blind hole of the implant, an abutment screw extends through the bore of the abutment, with an end of the abutment screw engaged in the abutment, and with the other end of the abutment screw extending out of the abutment and extending into and tightened in the blind hole of the implant by thread engagement, achieving secure coupling between the implant and the abutment.

However, there is no retaining or positioning structure between the abutment and the implant before the abutment is securely fixed in the blind hole of the implant by the abutment screw. Thus, the abutment is apt to fall out of the blind hole of the implant in a tooth implantation surgery of an upper tooth, causing inconvenience to the surgery and adversely affecting surgery efficiency. In severe cases, the abutment falls on and stimulates the tongue of the patient, such that the patient swallows the abutment, resulting in medical disputes.

FIG. 1 shows a dental implant 9 including an implant 91, an abutment 92, and an abutment screw 93. A blind hole 911 extends axially from an end of the implant 91, forming an insertion portion 912 and a locking portion 913 in an interior of the implant 91. An annular flange 914 is formed on an inner periphery of the insertion portion 912. The locking portion 913 is closer to a closed end of the blind hole 911 than the insertion portion 912. The abutment 92 includes an implant coupling portion 921, a connection portion 922, a crown coupling portion 923, and an axially extending bore (not shown), with the implant coupling portion 921, the connection portion 922, and the crown coupling portion 923 connected to each other in the axial direction. The implant coupling portion 921 includes an annular groove 924 adjacent to a free end thereof. A plurality of resilient fingers 925 is provided between the annular groove 924 and the free end of the implant coupling portion 921. Each resilient finger 925 includes an outwardly protruding arcuate face. A notch 926 is formed between two adjacent resilient fingers 925. The resilient fingers 925 elastically deform when subjected to a radially-pressing external force and return to their initial position when the external force vanishes. An example of such a dental implant is disclosed in U.S. Pat. No. 7,338,286 (EP 1419746 B1).

In use of the dental implant 9, the implant 91 is implanted into an alveolar bone of a patient, and the implant coupling portion 921 of the abutment 92 is then inserted into the insertion portion 912 of the implant 91. During axial movement of the implant coupling portion 921 of the abutment 92 into the blind hole 911, and when the resilient fingers 925 come in contact with the annular flange 914, the annular flange 914 causes elastic deformation of the resilient fingers 925 and presses the resilient fingers 925 radially inward. After passing through the annular flange 914, the resilient fingers 925 return to their initial position, and the annular groove 924 of the abutment 92 is aligned with the annular flange 914. By abutting the resilient fingers 925 against a side of the annular flange 914, the whole abutment 92 can engage with the implant 91 and, is, thus, less likely to disengage from the implant 91 in the axial direction. Finally, the abutment screw 93 extends through the bore of the abutment 92 to fix an end of the abutment screw 93 in the abutment 92. The other end of the abutment screw 93 extends out of the abutment 92 and is tightened to the locking portion 913 of the implant 91 by thread engagement, achieving secure coupling between the implant 91 and the abutment 92.

When the abutment 92 of the dental implant 9 is being mounted, the abutment 92 and the implant 91 are engaged with each other before the abutment screw 93 is tightened, avoiding the abutment 92 from disengaging from the implant 91 after installation. However, it is difficult to form the delicate structures including the annular grooves 924, the resilient fingers 925 with outwardly protruding arcuate faces, and the notch 926 between two adjacent resilient fingers 925, because the size of each component of the dental implant 9 is relatively small. Thus, manufacturing of the abutment 92 becomes more difficult and has a low yield. Furthermore, formation of the annular flange 914 in the blind hole 911 of the implant 91 causes changes in the diameter of the blind hole 911 from the closed end to the open end thereof. Specifically, processing of the blind hole 911 is not as easy as the case of a blind hole having increasing diameters from an end to the other end. Rather, the diameter of the blind hole 911 is increased and then reduced and then enlarged, which requires special cutters and/or many processing procedures to form the desired shape. Thus, the implant 91 has the same disadvantages of difficult manufacturing and low yield. Furthermore, metal fatigue and breakage of the dental implant 9 are apt to occur clinically due to repeated coupling of the abutment 92 and the implant 91 by an inexperienced practitioner. Overall, the coupling structure of the dental implant 9 is too complicated, causing difficulties and low efficiency in manufacturing as well as a low yield. As a result, the dental implant 9 has high manufacturing costs.

Furthermore, the avoidance of disengagement of the abutment 92 of the dental implant 9 from the implant 91 can only be achieved after the resilient fingers 925 have passed through the annular flange 914 of the implant 91 to a position in which the annular groove 924 of the abutment 92 is aligned with the annular flange 914. Namely, when the abutment 92 is being coupled to the implant 91, the abutment 92 is not always in an engagement relation with the implant 91. If the practitioner fails to couple the abutment 92 to the predetermined location in the implant 91, it is possible for the abutment 92 to fall out of the implant 91. Further, as mentioned above, the annular flange 914 of the implant 91 and the resilient fingers 925 of the abutment 92 are delicate structures such that the practitioner can not exactly feel the resilient fingers 925 have passed the annular flange 914 of the implant 91. Thus, the dental implant 9 can not provide the expected result of avoiding the abutment 92 from falling out of the implant 91. Further, the dental implant 9 has a weak structure and is apt to fatigue.

SUMMARY OF THE INVENTION

An objective of the present invention is to provide a bone implant including an easy engagement arrangement between an implant and an abutment thereof, reducing the manufacturing costs and increasing the structural strength.

Another objective of the present invention is to provide a bone implant including an implant and an abutment, with the abutment and the implant retained in a mutually engaged relation with each other while mounting the abutment to the implant, effectively avoiding the abutment from falling out of the implant.

A further objective of the present invention is to provide a bone implant having an increased structural strength to reduce the risk of fatigue.

The present invention fulfills the above objectives by providing a bone implant including an implant, an abutment, and an abutment screw. The implant includes an implantation end and a connection end. The implant further includes an outer thread extending between the implantation end and the connection end. The implant further includes a blind hole formed in the connection end and extending in an axial direction, defining an abutment receiving section and a locking section in an interior of the implant. The abutment receiving section includes an anti-rotation portion having a hole, with the hole having non-circular cross sections perpendicular to the axial direction. The anti-rotation portion has a minimal inner width perpendicular to the axial direction. The locking section adjoins a closed end of the blind hole. The abutment includes an elastic, deformable portion, a connection portion, and a prosthesis engagement portion. The elastic, deformable portion, the connection portion, and the prosthesis engagement portion are connected to each other in the axial direction. The abutment further includes a bore extending through the elastic, deformable portion, the connection portion, and the prosthesis engagement portion in the axial direction. The elastic, deformable portion includes a plurality of resilient plates spaced from each other. A slit is formed between two adjacent resilient plates. The elastic, deformable portion has a maximal outer width when the plurality of resilient plates is not subjected to a force. The maximal outer width is larger than the minimal inner width. The elastic, deformable portion is aligned and engages with the anti-rotation portion of the implant. The abutment screw includes a head end positioned in the bore of the abutment. The abutment screw further includes a locking end engaged with the locking section of the implant.

Preferably, each of the plurality of resilient plates includes a free end having an inclined face. The elastic, deformable portion has decreasing outer diameters toward the free ends of the plurality of resilient plates.

Preferably, the interior of the implant includes an abutment stop section between the abutment receiving section and the locking section. The elastic, deformable portion of the abutment abuts the abutment stop section.

Preferably, the locking section has an inner diameter perpendicular to the axial direction of the implant smaller than an inner diameter of the abutment stop section perpendicular to the axial direction, forming a first abutment face. Each of the plurality of resilient plates has an end face abutting the first abutment face. The inner diameter of the abutment stop section is smaller than the minimal inner width of the abutment receiving section, forming a second abutment face. The inclined face of each of the plurality of resilient plates abuts the second abutment face.

Preferably, the abutment receiving section of the implant further includes a guiding portion. The anti-rotation portion is closer to the locking section of the implant than the guiding portion. The guiding portion has increasing diameters from a location adjoining the anti-rotation portion toward an open end of the blind hole to form a conic surface.

Preferably, the connection portion of the abutment includes a small diameter section and a large diameter section. The small diameter portion is connected to the elastic, deformable portion, and the large diameter portion is connected to the prosthesis engagement portion.

Preferably, the elastic, deformable portion of the abutment is aligned with the anti-rotation portion of the abutment receiving section of the implant. The small diameter section of the connection portion of the abutment is aligned with the guiding portion of the abutment receiving section of the implant. The large diameter section of the connection portion of the abutment is exposed outside of the implant.

Preferably, the hole of the anti-rotation portion of the implant includes regular polygonal cross sections perpendicular to the axial direction of the implant.

By the above structure, the bone implant according to the present invention provides an easy mutual engagement between the implant and the abutment to avoid the abutment from falling out of the implant before the abutment screw securely engages with the abutment. Compared to conventional bone implants, the bone implant according to the present invention is easy to manufacture, simplifying the processing procedures and increasing the yield. Thus, the manufacturing costs are significantly reduced to largely increase the competitiveness of the bone implant in the market. Furthermore, when the abutment is being engaged with the implant of the bone implant according to the present invention, the abutment is kept in an engagement relation with the implant to increase the operational convenience while effectively avoiding the abutment from falling out of the implant. The simple engagement structure of the bone implant according to the present invention possesses enhanced structural strength to reduce the risk of fatigue and breakage, increasing the service life of the bone implant.

The present invention will become clearer in light of the following detailed description of illustrative embodiments of this invention described in connection with the drawings.

DETAILED DESCRIPTION OF THE INVENTION

Figure 1:
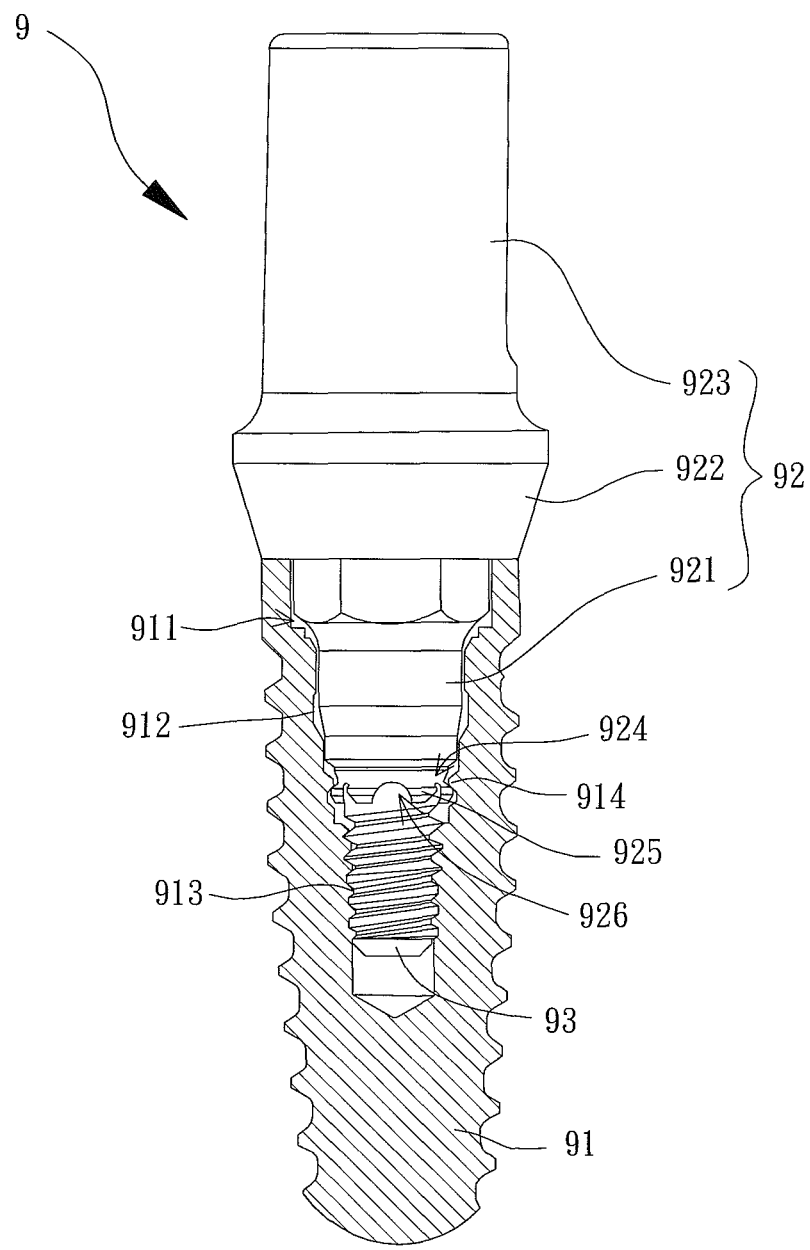
FIG. 1 is a cross sectional view of a conventional dental implant.
Figure 2:
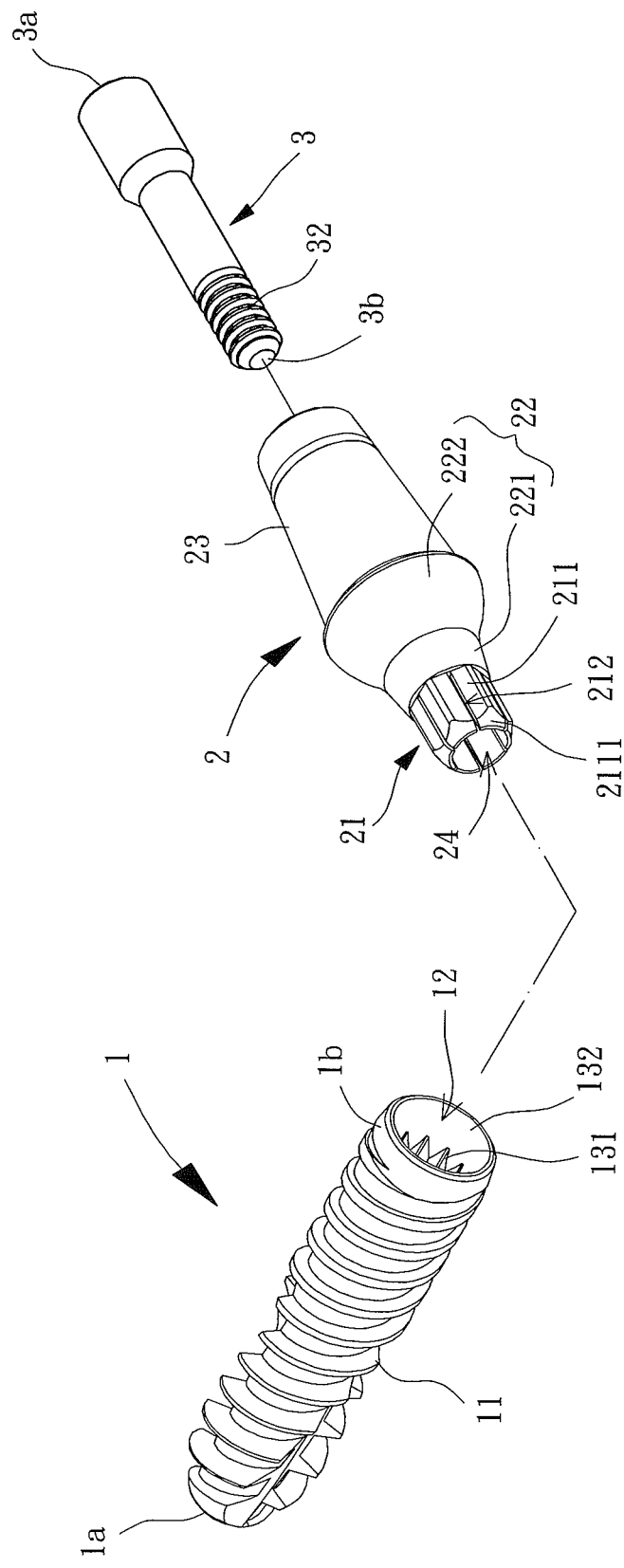
FIG. 2 is an exploded, perspective view of a dental implant according to the present invention.

FIG. 2 shows a preferred embodiment of a dental implant according to the present invention. The dental implant according to the present invention generally includes an implant 1, an abutment 2, and an abutment screw 3. The abutment 2 is coupled to the implant 1, and the abutment screw 3 extends through the abutment 2 to securely engaging the implant 1 with the abutment 2. The implant 1 is adapted to be fixed to a bone. The abutment 2 is adapted to engage with a prosthesis such as a dental crown, artificial ear, or artificial finger. The shape and type of the implant 1 and the abutment 2 can be changed according to needs, which can be appreciated by one having ordinary skill in the art. The present invention will now be set forth with reference to an example of a bone implant for a dental crown without limiting purposes.

Figure 3:
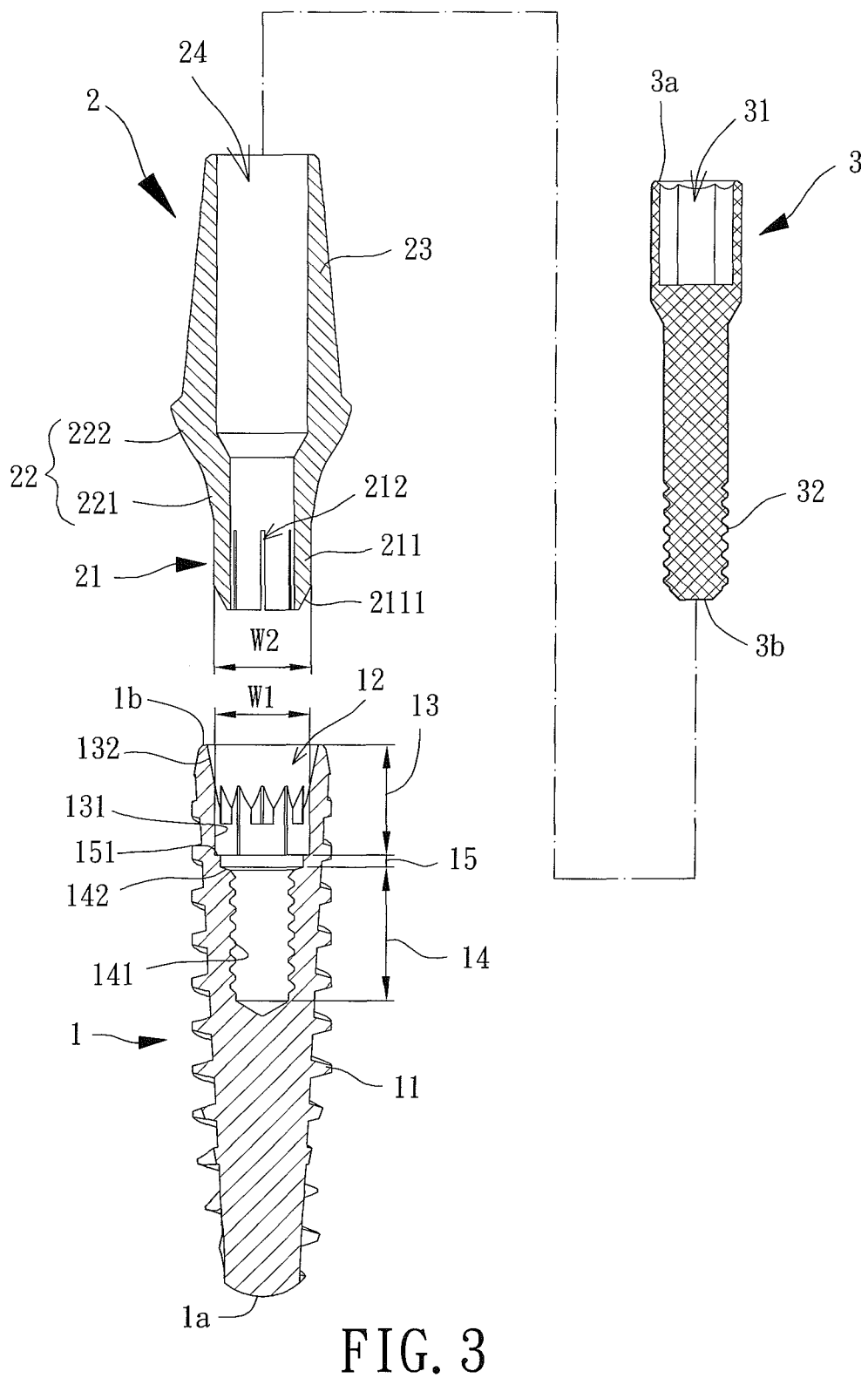
FIG. 3 is an exploded, cross sectional view of the dental implant according to the present invention.

With reference to FIGS. 2 and 3, the implant 1 includes an implantation end 1a and a connection end 1b. The implantation end 1a is adapted to be implanted into an alveolar bone of a patient at a location of a missing tooth. The implant 1 further includes an outer thread 11 extending between the implantation end 1a and the connection end 1b. The implant 1 further includes a blind hole 12 formed in the connection end 1b and extends in an axial direction, defining an abutment receiving section 13 and a locking section 14 in an interior of the implant 1. The abutment receiving section 13 receives a portion of the abutment 2. The locking section 14 adjoins a closed end of the blind hole 12, and the abutment screw 3 is tightened in the locking section 14. Preferably, the interior of the implant 1 includes an abutment stop section 15 between the abutment receiving section 13 and the locking section 14. The elastic, deformable portion 21 of the abutment 2 abuts the abutment stop section 15 to limit the engagement depth of the abutment 2 relative to the implant 1.

In this embodiment, the abutment receiving section 13 includes an anti-rotation portion 131 and a guiding portion 132. The anti-rotation portion 131 is closer to the locking section 14 of the implant 1 than the guiding portion 132. The anti-rotation portion 131 includes a hole having non-circular cross sections perpendicular to the axial direction, such that the abutment 2 can not rotate about an axis of the implant 1 after the abutment 2 is received in the anti-rotation portion 131 of the abutment receiving section 13. Preferably, the hole of the anti-rotation portion 131 of the implant 1 includes regular polygonal cross sections (such as, but not limited to, regular hexagonal cross sections) perpendicular to the axial direction of the implant 1, allowing adjustment of an angular position of the abutment 2 relative to the implant 1. Furthermore, the anti-rotation portion 131 has a minimal inner width W1 perpendicular to the axial direction of the implant 1. The guiding portion 132 has increasing diameters from a location adjoining the anti-rotation portion 131 toward an open end of the blind hole 12 to form a conic surface for guiding the abutment 2 into the blind hole 12 along the axial direction of the implant 1.

The locking section 14 of the implant 1 includes an inner thread 141. The locking section 14 has an inner diameter perpendicular to the axial direction of the implant 1 smaller than an inner diameter of the abutment stop section 15 perpendicular to the axial direction, forming a first abutment face 142. The inner diameter of the abutment stop section 15 is smaller than the minimal inner width W1 of the abutment receiving section 13, forming a second abutment face 151 on a location of the abutment stop section 15 adjoining the abutment receiving section 13.

The abutment 2 includes an elastic, deformable portion 21, a connection portion 22, and a prosthesis engagement portion 23. The elastic, deformable portion 21, the connection portion 22, and the prosthesis engagement portion 23 are connected to each other in the axial direction. The abutment 2 further including a bore 24 extending through the elastic, deformable portion 21, the connection portion 22, and the prosthesis engagement portion 23 in the axial direction. The elastic, deformable portion 21 includes a plurality of resilient plates 211 spaced from each other. A slit 212 is formed between two adjacent resilient plates 211. Thus, each resilient plate 211 can elastically deform inward in a radial direction perpendicular to the axial direction. The elastic, deformable portion 21 has a maximal outer width W2 when the resilient plates 211 are not subjected to a force. The maximal outer width W2 is larger than the minimal inner width W1. Each resilient plate 211 includes a free end having an inclined face 2111. The elastic, deformable portion 21 has decreasing outer diameters toward the free ends of the resilient plates 211 to provide smoother movement of the elastic, deformable portion 21 of the abutment 2 into the abutment receiving section 13. Furthermore, each resilient plate 211 is thinner at its free end, such that the free end is liable to deform when subjected to a force, creating an instant pressing effect.

The connection portion 22 of the abutment 2 includes a small diameter section 221 and a large diameter section 222. The small diameter portion 221 is connected to the elastic, deformable portion 21, and the large diameter portion 222 is connected to the prosthesis engagement portion 23. When the abutment 2 engages with the implant 1, both of the elastic, deformable portion 21 and the small diameter section 221 of the connection portion 22 of the abutment 2 are received in the abutment receiving section 13 of the implant 1. The large diameter section 222 of the connection portion 22 is exposed outside of the implant 1. The inner diameter of the bore 24 at the small diameter portion 221 is smaller than the inner diameter of the bore 24 at the large diameter portion 222, such that an end of the abutment screw 3 can be positioned in an adjoining area between the small diameter section 221 and the large diameter section 222. A dental crown (not shown) can be coupled with the prosthesis engagement portion 23 of the abutment 2. The shape of the prosthesis engagement portion 23 can be changed according to needs.

The abutment screw 3 includes a head end 3a and a locking end 3b. The head end 3a includes a coupling hole 31 for securely receiving a tool (not shown) that can be used to drive the abutment screw 3 to rotate about an axis of the abutment screw 3. The locking end 3b includes an outer thread 32 for thread engagement with the inner thread 141 of the implant 1.

Figure 4:
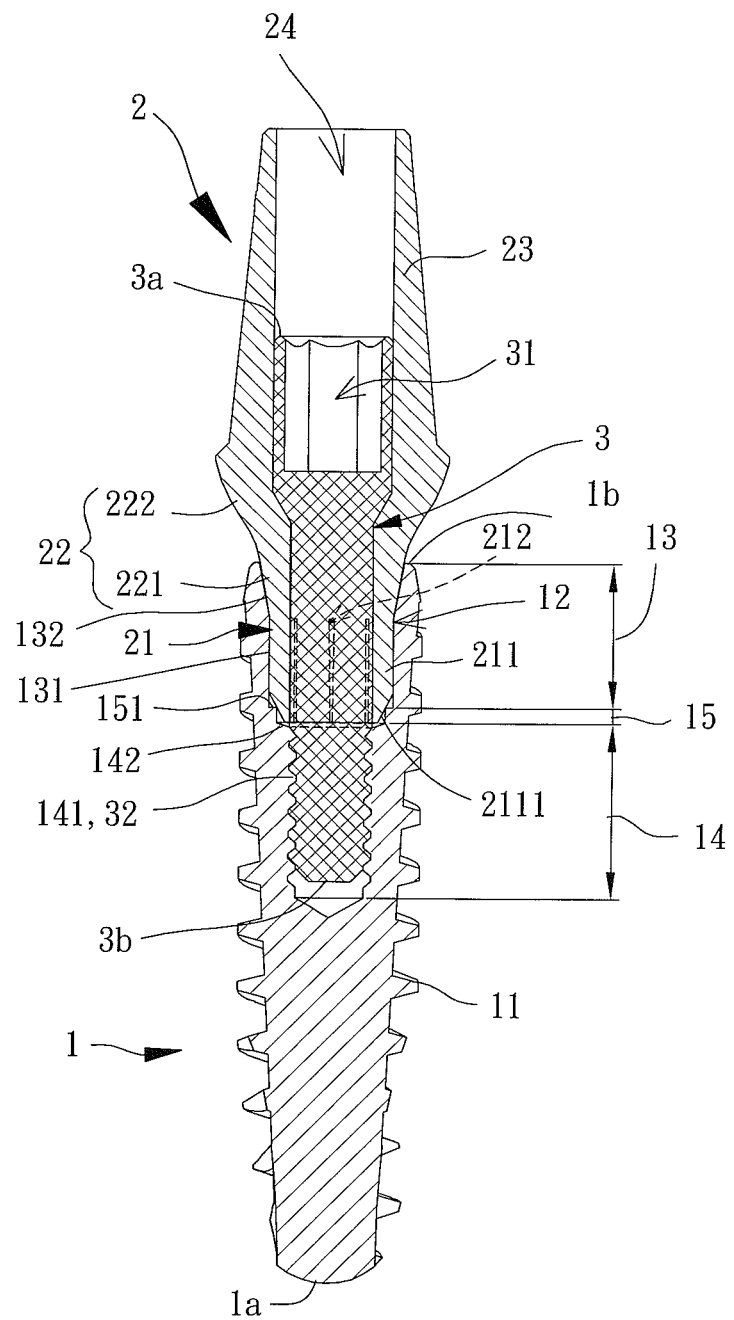
FIG. 4 is a cross sectional view of the dental implant according to the present invention.

With reference to FIGS. 3 and 4, when the bone implant according to the present invention is used in a tooth implantation surgery, the implant 1 is firstly implanted into an alveolar bone of a patient at a location of a missing tooth. Then, the elastic, deformable portion 21 of the abutment 2 is inserted into the blind hole 12 until the elastic, deformable portion 21 is aligned with and engages with the anti-rotation portion 131 of the implant 1. Next, the abutment screw 3 is inserted into the bore 24 of the abutment 2 to position the head end 3a of the abutment screw 3 in the bore 24 of the abutment 2, with the locking end 3b of the abutment screw 3 extending out of the elastic, deformable portion 21 of the abutment 2. A tool is coupled to the abutment screw 3 and is driven to rotate the abutment screw 3 about its axis to engage the outer thread 32 of the abutment screw 3 with the inner thread 141 of the implant 1, achieving secure engagement between the implant 1 and the abutment 2, with the elastic, deformable portion 21 aligned with the anti-rotation portion 131 of the abutment receiving section 13 of the implant 1, and with the small diameter section 221 of the connection portion 22 aligned with the guiding portion 132 of the abutment receiving section 13. After the wound heals, a dental crown is mounted to the prosthesis engagement portion 23 to finish the tooth implantation surgery.

During axial movement of the elastic, deformable portion 21 of the abutment 2 into the blind hole 12, since the maximal outer width W2 of the elastic, deformable portion 21 of the abutment 2 is larger than the minimal inner width W1 of the anti-rotation portion 131 of the implant 1, and after the free ends of the resilient plates 211 of the elastic, deformable portion 21 extend into the anti-rotation portion 131 of the implant 1, each resilient plate 211 is pressed by an inner wall of the anti-rotation portion 131 and, thus, moves radially inward and elastically deforms. This permits the elastic, deformable portion 21 of the abutment 2 to continuously move into the anti-rotation portion 131 of the implant 1 until the end face of each resilient plate 211 abuts the first abutment face 142 and until the inclined face 2111 of each resilient plate 211 abuts the second abutment face 151. Due to the elastic returning force of each resilient plate 211, the resilient plates 211 of the elastic, deformable portion 21 of the abutment 2 keep pressing against the inner wall of the anti-rotation portion 131 during the entire axial movement of the abutment 2. Thus, no matter if the free ends of the resilient plates 211 of the elastic, deformable portion 21 have reached the abutment stop section 15, the abutment 2 will not fall out of the blind hole 12.

In view of the foregoing, the bone implant according to the present invention provides an easy mutual engagement between the implant 1 and the abutment 2 to avoid the abutment 2 from falling out of the implant 1 before the abutment screw 3 securely engages with the abutment 2. Compared to conventional bone implants, the bone implant according to the present invention is easy to manufacture, simplifying the processing procedures and increasing the yield. Thus, the manufacturing costs are significantly reduced to largely increase the competitiveness of the bone implant in the market.

When the abutment 2 is being engaged with the implant 1 of the bone implant according to the present invention, the abutment 2 is kept in an engagement relation with the implant 1 to increase the operational convenience while effectively avoiding the abutment 2 from falling out of the implant 1.

The simple engagement structure of the bone implant according to the present invention possesses enhanced structural strength to reduce the risk of fatigue and breakage, increasing the service life of the bone implant.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A bone implant comprising:
    an implant including an implantation end and a connection end, wherein the implant further includes an outer thread extending between the implantation end and the connection end, wherein the implant further includes a blind hole formed in the connection end and extending in an axial direction, defining an abutment receiving section and a locking section in an interior of the implant, wherein the interior of the implant includes an abutment stop section between the abutment receiving section and the locking section, wherein the abutment receiving section includes an anti-rotation portion having a hole, wherein the hole has non-circular cross sections perpendicular to the axial direction, wherein the anti-rotation portion has a minimal inner width perpendicular to the axial direction, and wherein the locking section adjoins a closed end of the blind hole;
    an abutment including an elastic, deformable portion, a connection portion, and a prosthesis engagement portion, wherein the elastic, deformable portion, the connection portion, and the prosthesis engagement portion are connected to each other in the axial direction, wherein the elastic, deformable portion of the abutment abuts the abutment stop section, wherein the abutment further includes a bore extending through the elastic, deformable portion, the connection portion, and the prosthesis engagement portion in the axial direction, wherein the elastic, deformable portion includes a plurality of resilient plates spaced from each other, wherein a slit is formed between two adjacent resilient plates, wherein each of the plurality of resilient plates includes an end face and a free end having an inclined face, wherein the elastic, deformable portion has a maximal outer width when the plurality of resilient plates is not subjected to a force, wherein the maximal outer width is larger than the minimal inner width, wherein the elastic, deformable portion is aligned and engaged with the anti-rotation portion of the implant, wherein the elastic, deformable portion has decreasing outer diameters toward the free ends of the plurality of resilient plates, wherein the locking section has an inner diameter perpendicular to the axial direction of the implant smaller than an inner diameter of the abutment stop section perpendicular to the axial direction, forming a first abutment face, wherein each of the plurality of resilient plates has the end face abutting the first abutment face, wherein the inner diameter of the abutment stop section is smaller than the minimal inner width of the abutment receiving section, forming a second abutment face, and wherein the inclined face of each of the plurality of resilient plates abuts the second abutment face; and
    an abutment screw including a head end positioned in the bore of the abutment, wherein the abutment screw further includes a locking end engaged with the locking section of the implant.

2. The bone implant as claimed in claim 1, wherein the abutment receiving section of the implant further includes a guiding portion, wherein the anti-rotation portion is closer to the locking section of the implant than the guiding portion, and wherein the guiding portion has increasing diameters from a location adjoining the anti-rotation portion toward an open end of the blind hole to form a conic surface.

3. The bone implant as claimed in claim 2, wherein the connection portion of the abutment includes a small diameter section and a large diameter section, wherein the small diameter section is connected to the elastic, deformable portion, and wherein the large diameter section is connected to the prosthesis engagement portion.

4. The bone implant as claimed in claim 3, wherein the elastic, deformable portion of the abutment is aligned with the anti-rotation portion of the abutment receiving section of the implant, wherein the small diameter section of the connection portion of the abutment is aligned with the guiding portion of the abutment receiving section of the implant, and wherein the large diameter section of the connection portion of the abutment is exposed outside of the implant.

5. The bone implant as claimed in claim 1, wherein the hole of the anti-rotation portion of the implant includes regular polygonal cross sections perpendicular to the axial direction of the implant.

6. The bone implant as claimed in claim 2, wherein the hole of the anti-rotation portion of the implant includes regular polygonal cross sections perpendicular to the axial direction of the implant.

* * * * *